United States Patent
Hammes

(10) Patent No.: US 10,823,801 B2
(45) Date of Patent: Nov. 3, 2020

(54) METHOD AND MAGNETIC RESONANCE APPARATUS FOR PROVIDING OPERATING PARAMETERS TO THE MAGNETIC RESONANCE APPARATUS

(71) Applicant: Siemens Healthcare GmbH, Erlangen (DE)

(72) Inventor: Martin Hammes, Erlangen (DE)

(73) Assignee: Siemens Healthcare GmbH, Erlangen (DE)

(*) Notice: Subject to any disclaimer, the term of this patent is extended or adjusted under 35 U.S.C. 154(b) by 0 days.

(21) Appl. No.: 16/264,787

(22) Filed: Feb. 1, 2019

(65) Prior Publication Data
US 2019/0235038 A1    Aug. 1, 2019

(30) Foreign Application Priority Data
Feb. 1, 2018    (EP) .................................... 18154727

(51) Int. Cl.
| | |
|---|---|
| *G01R 33/54* | (2006.01) |
| *G16H 10/20* | (2018.01) |
| *G06N 20/00* | (2019.01) |
| *A61B 5/055* | (2006.01) |
| *G16H 40/20* | (2018.01) |
| *G16H 40/63* | (2018.01) |

(52) U.S. Cl.
CPC ............ *G01R 33/543* (2013.01); *A61B 5/055* (2013.01); *G01R 33/546* (2013.01); *G06N 20/00* (2019.01); *G16H 10/20* (2018.01); *G16H 40/20* (2018.01); *G16H 40/63* (2018.01)

(58) Field of Classification Search
CPC .... G01R 33/543; G01R 33/546; G16H 40/63; G16H 40/20; G16H 10/20; G06N 20/00; A61B 5/055
See application file for complete search history.

(56) References Cited

U.S. PATENT DOCUMENTS

| | | | | |
|---|---|---|---|---|
| 4,707,661 | A * | 11/1987 | Hoenninger, III | G01R 33/54 324/309 |
| 5,606,258 | A * | 2/1997 | Hoenninger, III | G01R 33/54 324/309 |
| 2008/0091466 | A1* | 4/2008 | Butler | G06Q 10/06 705/2 |
| 2010/0094700 | A1 | 4/2010 | Kuth et al. | |
| 2012/0041909 | A1 | 2/2012 | Glaser-Seidnitzer et al. | |

OTHER PUBLICATIONS

Preim et al., "Medical Volume Data in Clinical Practice," Visualization in Medicine: Theory, Algorithms, and Applications, Chapter 4 (2007).
Varma, D.R., "Managing DICOM images: Tips and tricks for the radiologist," Indian Journal of Radiology and Imaging, vol. 26 (2012).

* cited by examiner

*Primary Examiner* — G. M. A Hyder
(74) *Attorney, Agent, or Firm* — Schiff Hardin LLP

(57) ABSTRACT

In a method and an imaging apparatus for creating an aggregation file on an MR scanner, operating parameters on the MR scanner are acquired by a computer, and are aggregated and structured in the computer into a predefined uniform format for creating an aggregation file.

16 Claims, 3 Drawing Sheets

METHOD AND MAGNETIC RESONANCE APPARATUS FOR PROVIDING OPERATING PARAMETERS TO THE MAGNETIC RESONANCE APPARATUS

BACKGROUND OF THE INVENTION

Field of the Invention

The present invention concerns a method for providing operating parameters of a magnetic resonance (MR) apparatus.

Description of the Prior Art

An MR apparatus (MR tomography apparatus) is a complex technical machine having a number of technical components. They are used to carry out imaging procedures for medical diagnostics and to represent the structure and function of the tissues and organs in the body.

MR imaging is based on the selective excitation of certain atomic nuclei in the examined tissue with phase synchronicity to a certain extent, by a combination of static and radio-frequency magnetic fields. During realization after the excitation emit a measurable signal in the form of an alternating voltage until the relaxation subsides. For this purpose, the MR scanner has a basic field magnet and a number of gradient coils in order to be able to give the spatial resolution to the MR signal. Furthermore, a radio-frequency (RF) system is required to excite the spins by the temporary application of an additional radio-frequency alternating field. The RF system includes a power amplifier and an extremely sensitive receiver. When the radio-frequency alternating field has been switched off, the transverse magnetization (excitation) decreases so the spins are again aligned parallel to the static magnetic field. For this so-called relaxation, the nuclear spins require a characteristic decay time. This is determined by the chemical compound and the molecular environment in which the precessing hydrogen nuclei are located. Therefore, the different types of tissue characteristically differ in their signals, resulting in different signal strengths (brightnesses) in the resulting image.

The signal of the excited nuclei is acquired by antennas in a local coil in which a voltage is induced, is then amplified (for example with a low-noise preamplifier LNA), and finally forwarded to the receiving electronics via a cable. Additional components can be used for further data acquisition. This enables more coil elements to be connected to an MRI receiving system than receivers are present. In this case, a switching matrix is installed between the receive antennas and the receiver. This routes the currently active reception channels to the existing receivers. This makes it possible to connect more coil elements than receivers are present since, with full body coverage, it is only necessary to read out those coils that are located in the FoV (field of view) or in the homogeneity volume of the magnet.

MR devices in use differ in terms of their design and the functions that can be executed thereby. For example, depending upon the positioning and number of gradient coils, it is possible to select different anatomical body areas, and hence different medical questions. The possible configurations for a scan protocol for the examination of a patient are also influenced, for example, by the strength of the basic field magnet, the magnetic field homogeneity generated thereby, the number of channels, and the size of the FOV.

Hence, in practice, it is important to obtain information about the technical equipment and configuration of the particular MR apparatus (scanner) that is to be used, for example, with the aforementioned components (B0 coil, gradient coils, RF antennas, channels etc.), which represent the available capabilities of the MR scanner, and to make them available on an interoperable basis, in order to enable enhanced planning of the use of the MR device.

In the MR systems used in the prior art, it is not possible to automatically read this information directly from the components. This means that clinical staff (radiologists, technicians) have to know the capabilities of the scanner that will be used, for appropriate patient planning. This individual and manual procedure has proven to be particularly difficult and error prone when it is necessary to manage several MR scanners with different equipment (for example in clinic chains or large hospitals). Hence, scheduling uses of these multiple apparatuses disadvantageously requires experienced staff.

SUMMARY OF THE INVENTION

An object of the present invention is to improve the operation of such a medical device, in particular an MR apparatus, in clinical use. In particular, it is an object to automate the technical planning of the MR apparatus. For this purpose, access to the necessary information regarding the operating parameters of the MR scanner is to be improved and made available on an interoperable basis.

The following describes how this object with reference to an MR scanner (or MR apparatus). However, it will be apparent to those skilled in the art that the solution can also be applied to other medical devices or modalities (CT, US, PET, etc.). The operating parameters then specify the technical properties and configurations of such respective devices.

According to a first aspect of the invention, the object is achieved by a method for creating an aggregation file on an MR scanner having the following steps.

Operating parameters representing the available technical properties and/or functionality data about an MR scanner are provided to a computer. Preferably, sensor data and data from components installed in the MR scanner are acquired and processed. The sensor data can originate, for example, from sensors in certain components of the MR scanner that indicate the position and number of gradient coils. It is possible to determine operating parameters from this sensor data and further data by execution of a detection algorithm in the computer. Other sensors can be used to determine the magnetic field strength from which the detection algorithm can determine further operating parameters with or without access to a database with association relationships.

The computer aggregates and structures the acquired operating parameters to a predefined uniform format so as to create the aggregation file.

The inventive method has the advantageous technical effect that the aggregation file has a predefined, uniformly structured format. This improves or even establishes interoperability between the MR devices (for example in the case of devices from different manufacturers). It is also possible to replace local and/or proprietary operating parameters in a simple and uncomplicated manner without further intermediary instances (for example for conversion). External systems and further non-proprietary MR devices are able to retrieve the necessary data actively in the form of the aggregation file (PULL operation) or receive said data passively (PUSH operation), for example by implementing a polling strategy with cyclic queries for changed or new operating parameters or changes to the aggregation file in order to process them.

Expressed generally, the invention relates to a uniform exchange format for internal operating parameters of medical devices. The exchange format is defined by specifications for creating an aggregation file. These specifications are read in and converted by a structuring algorithm in order to create the aggregation file.

Hence, the aggregation and structuring of the acquired operating parameters into the uniform format (the aggregation file) is preferably executed by means of the structuring algorithm. The structuring algorithm is able to read in default data for the format to be created from an external database. This has the advantage that the format can also be changed independently of the algorithm, which can be implemented on a computing unit on the MR scanner.

In an embodiment of the invention, the operating parameters are a number of the available coils, a type of the available coils, executable protocols, a magnetic field strength, a gradient field strength, a field homogeneity, a channel number and/or an image area (field of view—FOV). The operating parameters can relate to hardware parameters of the MR device and/or to software parameters, such as available, installed software licenses. This can enable all relevant technical properties of the system to be represented and acquired.

In a further embodiment of the invention, an induction algorithm executed by the computer automatically calculates the clinical question that can be answered on the MR scanner from the aggregation file created and/or directly from the operating parameters acquired. For the calculation, the induction algorithm can access a database in which associations between a respective clinical question and the technical device configurations required therefor (which are coded in the operating parameters) are stored. This greatly simplifies the operation of the MR scanner since this important information can thus be provided automatically and no longer requires the use of skilled personnel.

In another embodiment of the invention, with a defined clinical question, a scan-time algorithm is executed by the computer so as to automatically predict from the aggregation file was created and/or directly from the acquired operating parameters, how long an average scan time (examination duration) will be based on protocols and scan sequences to be executed. Thus, the aggregation file created can be used to automate and improve the execution of the scheduling of the usage of the device.

In a further embodiment of the invention, the operating parameters are calculated from local device data. Herein, this can relate to the duration of the examination (scan time), which is calculated based on available protocols. Further planning data (for example patient preparation time) and the calculated scan time can be accessed to achieve improved planning and utilization of the MR scanner. It is also possible to measure the preparation time, for example as the time between the registration of the patient and the start of the scan. This enables the scheduling to be improved. The calculated and/or measured data (for example preparation time, slot time) can be provided in the aggregation file thus greatly simplifying and improving the planning of a system of a plurality of MR scanners (for example in hospital). This can increase the efficiency of the operation of the MR device overall.

According to a further embodiment of the invention, an association between a respective answerable clinical question and a set of operating parameters of the MR scanner "required" therefor can be stored. This can take place centrally in a database. This achieves the technical advantage that the answerability of the clinical questions can be automated in that the information is read out of the aggregation file created in a simple manner.

According to a further embodiment of the invention, associations between a respective answerable clinical question and a set of "required" operating parameters of the MR scanner are learned using machine learning methods. For this, it is, for example, possible to use an artificial neural network (ANN) that has been trained in a training phase with training data. The ANN can have multiple layers. Machine learning is a self-adaptive algorithm. Deep learning, a subset of machine learning, utilizes a series of hierarchical layers or a hierarchy of concepts to carry out the process of machine learning. The artificial neural networks used thereby include structures, also called "neurons", which are interconnected like a network. The first layer of the neural network, the visible "input layer", processes raw data input, such as the acquired operating parameters of the MR device. The data input contains variables that can be observed, hence "visible layer". This first layer forwards its output to the next layer. This second layer processes the information from the previous layer and passes on the result to inner layers ("hidden layers"). The result is output in the visible "output layer", the last layer. This divides the desired data processing (here: the learning of associations between acquired operating parameters, further operating parameters calculated therefrom and clinical questions that can be answered thereby) into a series of nested simple associations. An ANN of this kind can be implemented on the processor. The ANN can be used to predict examination data for the MR device. For example, the ANN can be trained to provide a forecast of the scan duration and possibly the breath-holding time based on the acquired operating parameters.

According to a further embodiment of the invention, the step of aggregating and structuring comprises a conversion of the acquired operating parameters. This has the advantage that the aggregation file can be provided as non-proprietary and hence independently of a specific format. This improves the interoperability of the method.

In another embodiment of the invention, the operating parameters are determined based on sensor data and/or from electronic data of the MR scanner and the components by execution of a detection algorithm. The sensors can be of different types and, for example, acquire the installation situation (for example of coils) and the configuration of the device. The electronic data is available locally on the MR device (stored locally) and/or can be read in from external instances (for example PACS, RIS) via network interfaces. The electronic data can be read out from the components of the scanner via an internal bus or communication system.

According to a further embodiment of the invention, the aggregation file is stored locally on the MR scanner. It can be transferred to external instances. Herein, two variants of the invention are provided. A first solution is that the scanner sends the aggregation file created actively according to a push system—for example via email or with a PUSH message. In a second solution, PULL logic is used. This has the advantage that the distribution list of recipients does not have to be administered on the actual scanner (which functions as the sender of the aggregation file created). This means that the requesting systems retrieve the aggregation file and this is thus provided passively on the sending node on request. In the event of changes to the system, the corresponding information is distributed by PUSH.

The above object also is achieved in accordance with the invention by a non-transitory, computer-readable data storage medium encoded with programming instructions that, when the storage medium is loaded into a computer, cause the computer to implement any or all embodiments of the method according to the invention, as described above.

In a further aspect, the invention encompasses to an MR-based system with at least one MR scanner and at least one computer that is configured to process operating parameters of the MR scanner and wherein the operating parameters are provided in an aggregation file which was created according to one of the above-described embodiments of the method.

The following describes the terminology used in this application in more detail.

The term 'operating parameters' combines the technical or physical capabilities of the MR device. These include the technical configuration of the device and in particular information as to how long a certain acquisition takes on a certain MR device, the effort required (for example for shimming or patient positioning), the available licenses and coils, in order to be able to carry out certain scans at all, etc. The operating parameters represent the technical properties of the MR system and can also include functionality data (the functions that can be executed on the device). The operating parameters are, as a rule, available locally on the device. They can be read in from a file. The operating parameters can be acquired based on sensor data originating from sensors in the respective components of the device.

Aggregation means a coordinated combination of the acquired operating parameters. Since the operating parameters occur at different places in the device, these first have to be collected at a central location (for example by all the sensors with the respective associated data processing unit).

The format relates to the logical structure of the aggregation file and in particular to a sequence of the entries of the operating parameters. Herein, preferably a uniform format can be defined for the type of the operating parameters (unit, format of the parameters, for example time expressed in seconds or milliseconds, etc.). Proprietary or device-specific information is preferably formatted in a non-proprietary and device-independent format. The specifications for the logical structure of the aggregation file can be defined as a standard in order to facilitate or simplify data exchange between different systems. The standard or the specifications for the format can be stored in a central database.

A "clinical question" is an electronic dataset that represents the clinical examination to be performed, i.e. for example, what can be examined in which body region and for which type of patients (for example adults, children, people with active/passive implants, pregnant women, etc.) a corresponding examination can be performed. Examples of possible questions are, for example: stroke, suspected tumor, multiple sclerosis, Alzheimer's disease, etc. Depending upon the functionality of the MR scanner and the configuration thereof and the installed components, it is possible for different clinical questions to be answered. For each clinical question, it is necessary for an executable protocol and the components required (available coils etc.) for the execution of the protocol to be stored, as well as information as to whether the clinical question cannot be answered for certain patients (for example, for safety reasons for implants). It is then necessary to read out the time duration and, for example, the breath-holding time. The association of the protocol to the clinical question can be performed either by the manufacturer on delivery of the system or by the customer. The protocols are in turn influenced by the MR sequences, coils and further sensors (for example respiratory sensors, cardiac triggering sensors) available and used in the protocol. These are acquired by sensors. In addition, the configuration of the protocol is influenced by the basic HW characteristics of the scanners (field strength, field homogeneity, FOV, number of channels etc.).

DESCRIPTION OF THE PREFERRED EMBODIMENTS

Figure 1:
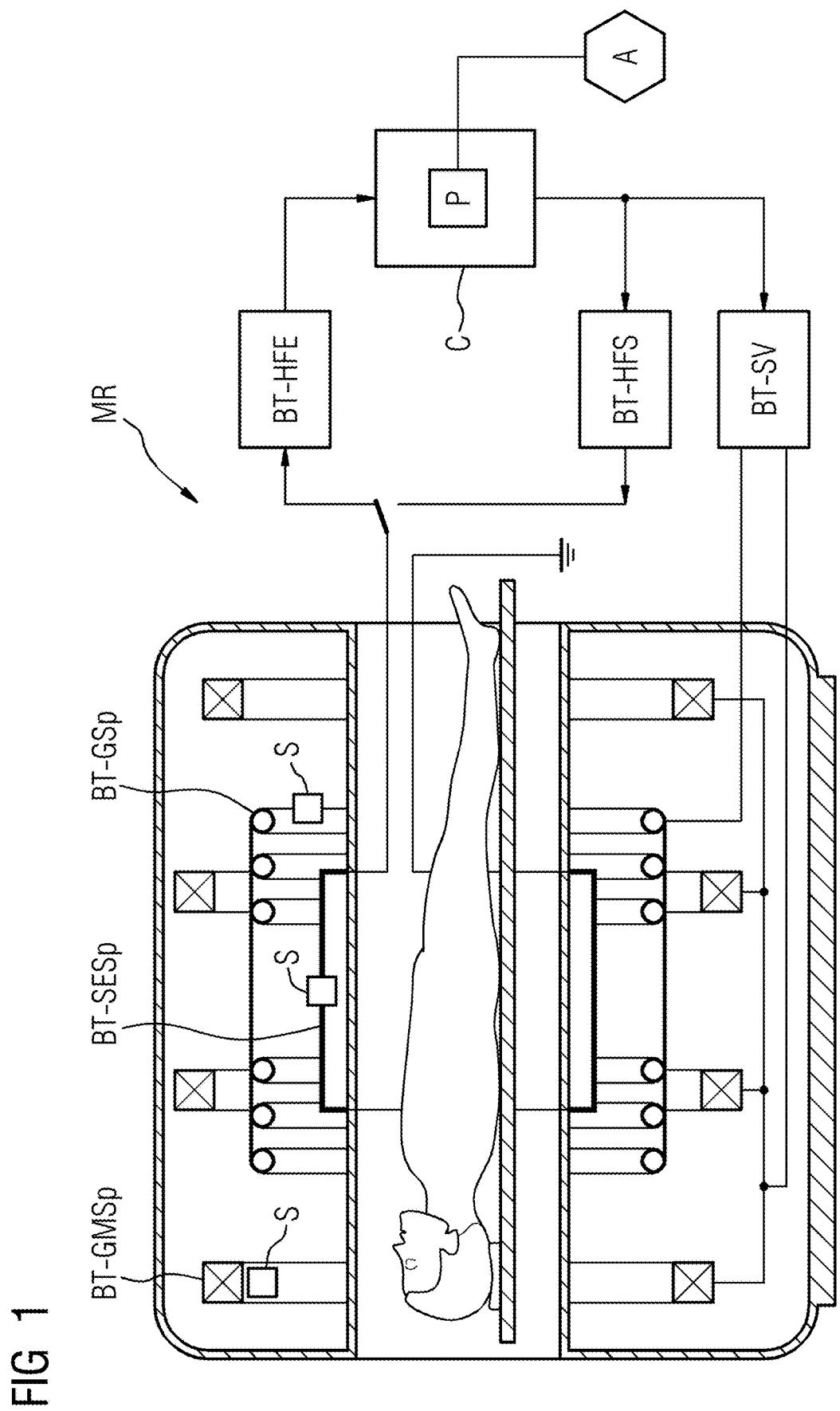
FIG. 1 schematically illustrates an MR system designed to create an aggregation file.

FIG. 1 is a schematic overview of an MR device MR with different components BT that include a basic magnetic field coil BT-GMSp, a plurality of gradient coils BT-GSp for spatial resolution and RF transmitting and receiving coils BT-SESp and an RF receiver component BT-HFE and an RF transmitter component BT-HFS. This is only a schematic representation and hence it is evident to the person skilled in the art that further components BT (not shown in FIG. 1), such as, for example, shim coils for homogenizing the magnetic field etc. will be used. As is shown in FIG. 1, sensors S can be arranged on all or selected components BT in order to acquire the existence, position, nature (for example type), arrangement and/or further technical properties of the respective component BT. A high-performance computer can be connected to the MR scanner MR as a computer unit C by means of an appropriate data connection.

Figure 2:
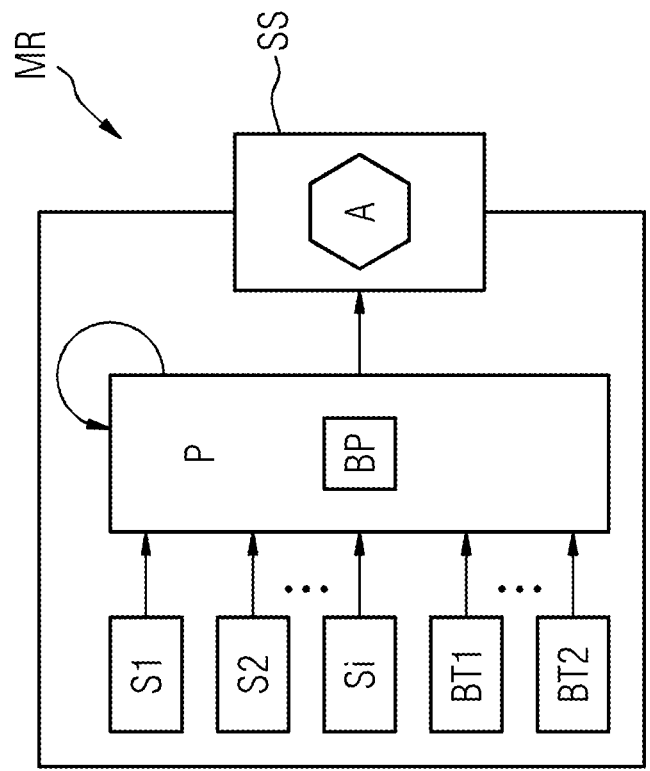
FIG. 2 is a block diagram of an MR apparatus for creating an aggregation file according to a preferred embodiment of the invention.

FIG. 2 shows the MR scanner MR with further modules. A processor P that functions as a computing unit is installed on the MR scanner MR. The aforementioned sensors S1, S2,—Si supply the acquired sensor data to the processor P. The sensor data can represent the position and type of a coil. The processor P can determine or calculate the operating parameters BP from the acquired sensor data directly or by means of a detection algorithm. Furthermore, the processor P receives data directly from the components BT. The processor P can calculate further operating parameters BP from the acquired data by means of the detection algorithm. In FIG. 2, this is represented by the arrow directed by the processor P onto itself. Therefore, further operating parameters BP are calculated from the data that is acquired and/or already present in order to aggregate all the collected data as operating parameters BP. The operating parameters preferably represent information on: available local coils, available software licenses on the computer C, basic scanner functionalities (for example, field strength, gradient strength etc.). The operating parameters BP aggregated in this way are structured according to a predefined format and used in this uniformly structured format to create an aggregation file A. The aggregation file A can be forwarded via a network interface SS to external instances. The fact that the aggregation file A has a uniformly structured format ensures interoperability between different MR devices MR, which, for the implementation of this invention, can also originate from different manufacturers.

Figure 3:
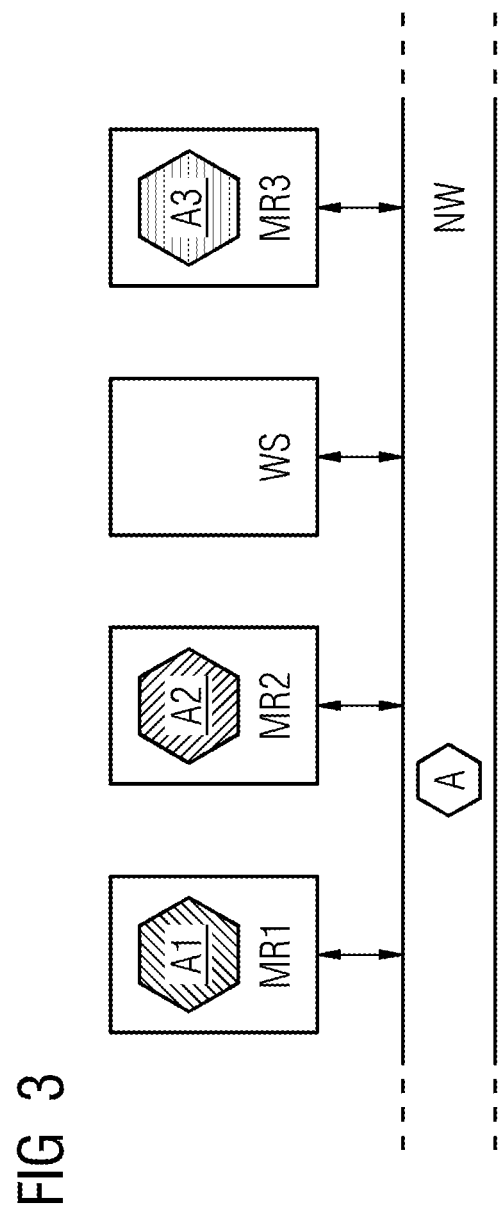
FIG. 3 is a flowchart of the method according to a preferred embodiment of the invention.

FIG. 3 shows an MR system with a number of MR devices MR1, MR2, MR3 and a workstation identified with the reference letters WS. Each MR device MR1, MR2, MR3 creates a device-specific aggregation file A1, A2, A3, which can be communicated via the network NW and, for example, be read in by the external workstation WS (PULL or PUSH operation). In FIG. 3, the shape of the aggregation file A indicates the uniform format of said file. Each aggregation file A is represented as a hexagon. This is to represent the uniform format of all aggregation files A. However, the data stored in the aggregation file A is specific to the MR device and specific to the configuration and differs from file to file. In FIG. 3, the different data content is identified by different hatching with the same shape (format) of the aggregation file A.

Figure 4:
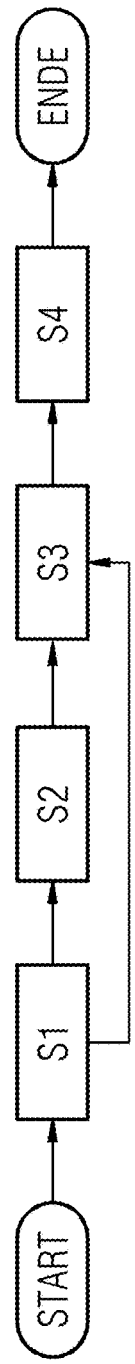
FIG. 4 illustrates a system of multiple medical devices that create and exchange aggregation files.

FIG. 4 is a flowchart of the method according to the invention. When the method for creating the aggregation file A on the MR scanner MR has been started, the operating parameters BP with the available properties and/or functionality data are acquired on the MR scanner MR. For this, it is possible for sensor data that was acquired on sensors S to be read in. The sensors S are arranged on the components BT of the MR device MR that are relevant for the operating parameters and in particular relevant for the questions as to which clinical questions can be answered on the device MR. In step S2, further operating parameters BP are calculated from the acquired and calculated data. However, step S2 is optional if a more comprehensive image is to be acquired in the aggregation file A. In step S3, the acquired and calculated operating parameters BP are aggregated and structured in a predefined, uniform format in order then to create the aggregation file A in step S4. The method can then be repeated or terminated.

Figure 5:
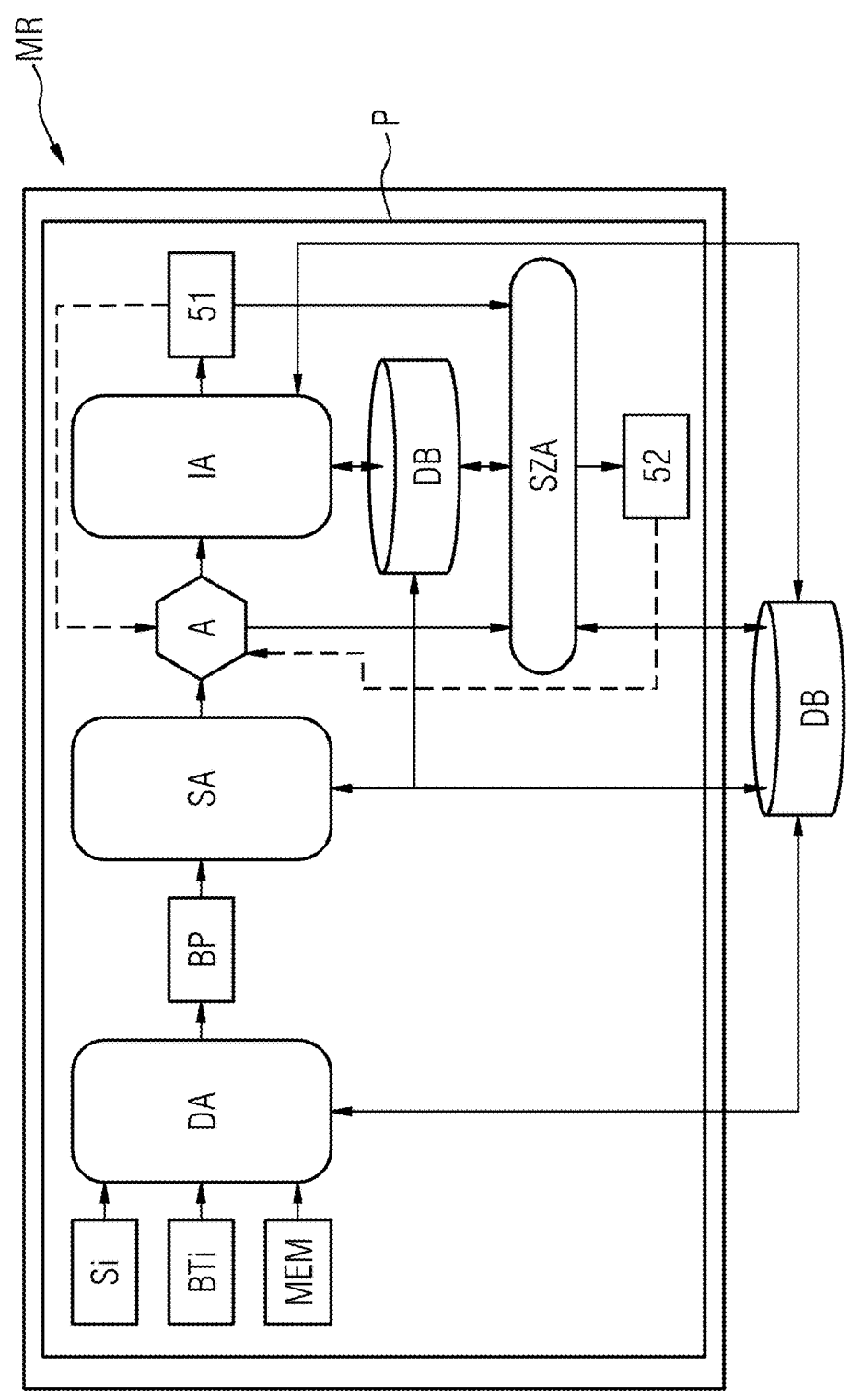
FIG. 5 schematically illustrates a processor for creating an aggregation file according to a further preferred embodiment of the invention.

FIG. 5 shows an MR apparatus MR with the processor P. At least one detection algorithm DA, which in this exemplary embodiment of the invention is embodied to provide operating parameters BP (to acquire them directly and/or calculate them) is implemented on the processor P. At least one further algorithm, the structuring algorithm SA, is implemented on the processor P. The structuring algorithm SA is used to structure the aggregated operating parameters BP in accordance with predefined specifications, in particular in a uniform format. For this purpose, it is able to access specifications stored in a central database DB. The structuring algorithm SA creates the aggregation file A.

In a simple embodiment of the invention, the possible further algorithms described in the following are implemented not on the processor P, but on external computer-based instances that have more computing power.

In a more complex embodiment of the invention, as depicted in FIG. 5, it is also possible for an indication algorithm IA and/or a scan-time algorithm SZA to be implemented on the processor P. The indication algorithm IA is used to calculate the answerable clinical question, which is identified with reference number 51 in FIG. 5. For the calculation, the indication algorithm IA can access the database DB in order to request the data required for the calculation. The calculated, answerable clinical questions 51 can be stored in the aggregation file A (depicted by a dashed line in FIG. 5).

The scan-time algorithm SZA is used to calculate a scan time, which is identified by reference number 52 in FIG. 5. The calculated scan time 52 can also be returned to the aggregation file (dashed line in FIG. 5).

The database DB is preferably situated outside the MR scanner MR and centrally for all MR scanners of the system.

In a preferred embodiment of the invention, the processor P is embodied to calculate the following datasets from the aggregation file A:

1. A list of the clinical questions 51 that can be answered with the MR scanner.
2. Meta-data on these clinical questions 51, in particular time-related data, such as, for example, the scan time 52 and/or typical preparation times for preparing a scan.
3. Downtime data indicating when the MR device MR is unavailable (for example during maintenance or servicing of the device) or other downtimes.

A significant advantage of the approach presented here is the fact that a standardized file, namely the aggregation file A, is provided on the MR system MR in which the technical capabilities of the MR system are depicted. This file can, for example, be addressed via a web interface (for example an IP address) (taking account of potential security requirements) and then makes the information on scanner capabilities available for third-party applications. The scanner capabilities can sometimes be depicted in the clinical question answerable with the scanner, i.e. with information as to which anatomical region is to be examined and the diagnosis in question (for example suspected stroke, tumor, MS, Alzheimer's disease, etc.). Further data can be requested externally by a user, for example the patient's breath-holding time, weight, height, etc. However, conversely, it is also possible—depending upon the capabilities of the scanner—for the length of the breath-holding time required to enable the patient to be examined with the available protocols on the scanner to be stored in the aggregation file A.

The time-related data can in particular be used for scheduling in order to plan future examinations on the device.

The aggregation file A can be extended by a full calendar function with an appropriate external interface. This embodiment of the invention makes it possible to return the aforementioned scheduling information to the scanner MR so that the scanner can provide more detailed information on its availability. In addition, the aggregation file A can be requested proactively and received by the HIS/RIS system in order, for example, to load and prepare the relevant data on scheduled patients in advance in order to improve performance. For example, it is possible to download the relevant patient information for patients scheduled for the next day on the night before the relevant day and for the scanner MR to prepare the corresponding protocols and settings in advance. This leads to advantages with respect to performance.

The aggregation file A is created in a uniform, structured language in order to store the scanner information in an appropriately defined file. It is also possible for this aggregation file A to be accessed by external instances and, for example, from the customer's (for example the hospital's) intranet and optionally even via the internet.

Finally, reference is made to the fact that the description of the invention and the exemplary embodiments should in principle be understood as being non-restrictive with respect to a specific physical implementation of the invention. All features explained and illustrated in conjunction with individual embodiments of the invention can be provided in different combinations in the subject matter according to the invention in order to implement the advantageous effects thereof at the same time.

Those skilled in the art will appreciate that the invention can be applied not only to MR devices but also to other medical device or modalities, such as CT, US. Furthermore, the components of the MR system can be implemented distributed over a plurality of physical products.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for producing an aggregation file with respect to a magnetic resonance (MR) data acquisition scanner, said method comprising:
   acquiring, using one or more sensors of the MR data acquisition scanner, sensor output data corresponding to one or more components of the MR data acquisition scanner;
   providing a computer with the sensor output data, and determining, by said computer, operating parameters based on the received sensor output data, wherein the operating parameters respectively define operation of the one or more components of an MR data acquisition scanner;
   in said computer, aggregating and structuring said operating parameters so as to form a predefined uniform format, and using said predefined uniform format to generate an aggregation file for said operating parameters of said MR data acquisition scanner; and
   making the aggregation file available from the computer in electronic form.

2. A method as claimed in claim 1 wherein said operating parameters include at least one parameter from the group consisting of a number of available coils of said MR data acquisition scanner, a type of said available coils, protocols that are executable by said MR data acquisition scanner, a basic magnetic field strength of a basic magnetic field produced by said MR data acquisition scanner, a gradient field strength of a gradient field produced by said MR data acquisition scanner, a field homogeneity of said basic magnetic field, a number of radio-frequency (RF) reception channels of said MR data acquisition scanner, and a volume within said MR data acquisition scanner from which MR data are acquired.

3. A method as claimed in claim 1 comprising, in said computer, using said aggregation file to formulate a clinical question that can be answered by operation of said MR data acquisition scanner.

4. A method as claimed in claim 1 comprising providing said operating parameters to said computer so as to include protocols that are executable by said MR data acquisition scanner and scan sequences that are executable by said data acquisition scanner, and, in said computer, using said aggregation file to calculate an average scan time for acquiring MR data according to said protocols and sequences.

5. A method as claimed in claim 1 comprising also providing said computer with scanner-specific data for said MR data acquisition scanner, and calculating said operating parameters in said computer from said scanner-specific data.

6. A method as claimed in claim 1 comprising providing said operating parameters to said computer so as to include protocols that are executable by said MR data acquisition scanner and scan sequences that are executable by said data acquisition scanner, and, in said computer, using said aggregation file to calculate an average scan time for acquiring MR data according to said protocols and sequences and storing said clinical question together with a set of operating parameters required for answering said clinical question by operation of said MR data acquisition scanner.

7. A method as claimed in claim 6 comprising generating said set of operating parameters in said computer by executing a machine learning algorithm.

8. A method as claimed in claim 1 comprising converting said acquired operating parameters in order to aggregate and structure said operating parameters so as to produce said aggregation file.

9. A method as claimed in claim 1 comprising storing said aggregation file in a memory that is locally associated with said MR data acquisition scanner.

10. A magnetic resonance (MR) apparatus comprising:
    an MR data acquisition scanner including one or more sensors associated with components of the MR data acquisition scanner; and
    a computer configured to:
       receive, from the one or more sensors, sensor output data associated with the components of the MR data acquisition scanner;
       determine operating parameters based on the received sensor output data, wherein the operating parameters respectively define operation of the components of said MR data acquisition scanner;
       aggregate and structure said operating parameters so as to form a predefined uniform format, and to use said predefined uniform format to generate an aggregation file for said operating parameters of said MR data acquisition scanner; and
       make the aggregation file available from the computer in electronic form.

11. A non-transitory, computer-readable data storage medium encoded with programming instructions, said storage medium being encoded with programming instructions and being loaded into a computer, and said programming instruction causing said computer system to:
    control one or more sensors associated with components of a magnetic resonance (MR) data acquisition scanner to detect information corresponding to one or more of the components and to generate sensor output data corresponding to the detected information;
    determine operating parameters based on the sensor output data, wherein the operating parameters respectively define operation of the components of an MR data acquisition scanner;
    aggregate and structure said operating parameters so as to form a predefined uniform format, and use said predefined uniform format to generate an aggregation file for said operating parameters of said MR data acquisition scanner; and
    make the aggregation file available from the computer in electronic form.

12. A method as claimed in claim 1 further comprising receiving data from the one or more components of an MR data acquisition scanner, wherein the operating parameters are determined based on the received sensor output data and the data received from the one or more components of an MR data acquisition scanner.

13. A method as claimed in claim 1 wherein determining said operating parameters uses a machine learning algorithm, the machine learning algorithm being configured to automatically adapt based on the sensor output data provided to the computer.

14. A method as claimed in claim 1 further comprising, in said computer, automatically determining one or more clinical questions, based on the aggregation file, answerable by operation of the MR data acquisition scanner.

15. A method as claimed in claim 1 further comprising, in said computer, automatically calculating an average scan time for acquiring MR data based on the aggregation file.

16. A method as claimed in claim 1 wherein acquiring the sensor output data comprises automatically acquiring the sensor output data using the one more sensors of the MR data acquisition scanner.

\* \* \* \* \*